United States Patent [19]

Goldfarb et al.

[11] Patent Number: 5,238,916
[45] Date of Patent: Aug. 24, 1993

[54] ONCOGENE ENCODED POLYPEPTIDE HAVING GROWTH FACTOR ACTIVITY AND METHODS OF USE THEREOF

[75] Inventors: Mitchell Goldfarb, River Edge, N.J.; Xi Zhan, New York, N.Y.

[73] Assignee: The Trustees of Columbia University in the City of New York, New York, N.Y.

[21] Appl. No.: 199,933

[22] Filed: May 27, 1988

Related U.S. Application Data

[63] Continuation-in-part of Ser. No. 56,137, May 29, 1987.

[51] Int. Cl.$^5$ .................. A61K 37/02; A61K 37/36; C07K 7/10; C07K 13/00
[52] U.S. Cl. ........................................ 514/2; 530/324; 530/399; 530/826
[58] Field of Search ........ 530/303, 350, 351, 324–326, 530/820, 826; 435/91; 536/27; 514/2

[56] References Cited

PUBLICATIONS

Abraham et al. 1986 "Nucleotide seq of a bovine clone . . ." Science 233:545–548. *
Jaye et al 1986 "Human endothelial cell growth factor . . ." Science 233:541–545.
Moore et al 1986 "Sequence topography & protein encoding potential . . ." EMBO J. 5:919–924.
Taira et al 1987 "cDNA sequence of human transforming gene . . ." PNAS 84:2980–2984.

Primary Examiner—Richard A. Schwartz
Assistant Examiner—S. L. Nolan
Attorney, Agent, or Firm—John P. White

[57] ABSTRACT

This invention provides a purified polypeptide having growth factor activity and a defined amino acid sequence. The invention also provides a purified nucleic acid molecule encoding the polypeptide. This invention further provides methods for producing the polypeptide as well as uses thereof. Finally, this invention provides methods for detecting the polypeptide.

6 Claims, 23 Drawing Sheets

FIGURE 5A
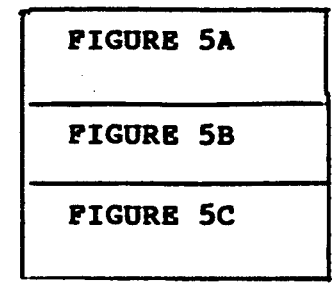

FIGURE 5C-1

```
ORF-1........................METSerThrArgCysGly                      6
         CCTCTCCCCTCTCTCTTCCCGAGGCTATGTCCACCCGGTGCGGC                44

GluAlaGlyGlnSerArgArgGlyThrGlnProHisArgGlyTyrArg                    21
GAGGCGGGCCAGAGCAGACGCAGCCGCACAGAGGGCTACAGA                          89

AlaGlnAsnGlnProTyrLysMetHisLeuGlyProProArgLeu                       36
GCCCAGAATCAGCCCTACAAGATGCACTTAGGACCCCGGCTG                         134
ORF-2.........

GluGluEND                                                           38
GAAGAATGAGCTTGTCCTTCCTCCTCCTCCTCTTCAGCCAC                          178
........METSerLeuSerPheLeuLeuLeuPheSerHis                           13

CTGATCCTCAGCGCGCTGGGCTCACGGGAGAAGCGTCTCGCCCCC                      223
LeuIleLeuSerAlaTrpAlaHisGlyGluLysArgLeuAlaPro                       28

AAAGGGCAACCCGGACCCGCTGCCACTGATAGGAACCCTAGAGGC                      268
LysGlyGlnProGlyProAlaAlaThrAspArgAsnProArgGly                       43
```

FIGURE 5C-2

```
TCCAGCAGCAGAGACAGCAGTAGCGCTATGTCTTCCTCTCT         313
SerSerSerArgGlnSerSerSerAlaMetSerSerSer            58

GCCTCCTCCTCCCCGCCAGCTTCTGGGCCAGCCAAGGAAGTGGC       358
AlaSerSerProAlaAlaSerLeuGlySerGlnGlySerGly         73

TTGGAGCAGAGCAGTTTCCAGTGGAGAGCCCTCGGGGCCGGACCGGC    403
LeuGluGlnSerSerPheGlnTrpSerLeuGlyAlaArgThrGly      88

AGCCTCTACTGCAGAGTGGGCATCGGTTTCCATCTGCAGATCTAC      448
SerLeuTyrCysArgValGlyIleGlyPheHisLeuGlnIleTyr      103

CCGGATGGCAAAGTCAATGGATCCCACGAAGCCAATATGTTAAGT      493
ProAspGlyLysValAsnGlySerHisGluAlaAsnMetLeuSer      118

GTTTTGGAAATATTTGCTGTGTCTCAGGGGATTGTAGGAATACGA      538
ValLeuGluIlePheAlaValSerGlnGlyIleValGlyIleArg      133
```

FIGURE 5C-3

```
GGAGTTTTCAGCAACAAATTTTAGCGATGTCAAAAAGGAAAA          583
GlyValPheSerAsnLysPheLeuAlaMetSerLysLysGlyLys       148

CTCCATGCCAAGTGCCAAGTTCACAGATGACTGCAAGTTCAGGGAG      628
LeuHisAlaSerAlaLysPheThrAspCysLysPheArgGlu          163

CGTTTTCAAGAAAATAGCTATATACCTATGCCTCAGCAATACAT        673
ArgPheGlnGluAsnSerTyrAsnThrTyrAlaSerAlaIleHis       178

AGAACTGAAAAAACAGGGGCGGAGTGGTATGTTGCCCTGAATAAA       718
ArgThrGluLysThrGlyArgGluTrpTyrValAlaLeuAsnLys       193

AGAGGAAAAGCCAAAACGAGGGTGCAGCCCCCGGGTTAAACCCCAG      763
ArgGlyLysAlaLysArgGlyCysSerProArgValLysProGln       208

CATATCTCTACCCATTTTCTTCCAAGATTCAAGCAGTCGGAGCAG       808
HisIleSerThrHisPheLysProArgPheLysGlnSerGluGln       223
```

FIGURE 5C-4

CCAGAACTTTCTTTCACGGTTACTGTTCCTGAAAAGAAAAATCCA 853
ProGluLeuSerPheThrValThrValProGluLysLysAsnPro 238

CCTAGCCCTATCAAGTCAAAAGATTCCCCTTTCTGCACCTCGGAAA 898
ProSerProIleLysSerLysIleProLeuSerAlaProArgLys 253

AATACCAACTCAGTGAAATACAGACTCAAGTTTCGCTTTGGATAA 943
AsnThrAsnSerValLysTyrArgLeuLysPheArgPheGlyEND 267

TATTAATCTTGGCCCTTGTGAGAAACCATTCTTTCCCCTCAGGAGT 988

TTCTATAGGTGTCTTCAGAGTTCTGAAGAAAATTACTGGACACA 1033

GCTTCAGCTATACTTACACTGTATTGAAGTCACGTCATTTGTTTC 1078

AGTGTGACTGAAACAAAATGTTTTTTGATAGGAAGGAAACTG 1120

FIGURE 6-1

```
FGF-3    (1)                      MSLSFLLLFFSHLILSAWA   (20)
hstKS3   (1)                      MSGPGTAAVALLPAVL      (16)

FGF-3    (21)   HGEKRLAPKGQPGPAATDRN                    (40)
hstKS3   (17)   LALLAPWAGRGGAAAPTAPN                    (36)

FGF-3    (41)   PRGSSRQSSSSAMSSSSAS                     (60)
hstKS3   (37)   GTLEAELERRWESLVALSLA                    (56)
int-2    (1)    MGLIWLLLSLLEPSWPT                       (18)
bFGF     (1)                                       MA   (2)

FGF-3    (61)   SSPAASLGSQGSGLEQSFQ                     (80)
hstKS3   (57)   RLPVAAQPKEAAVQSGAGDY                    (76)
int-2    (19)   TGPGTRLRRDAGGRGGVYEH                    (38)
bFGF     (3)    AGSITTLPALPEDGGSGAFP                    (22)
aFGF     (1)    MAEGEITTFTALTEKFNLP                     (19)
```

FIGURE 6-2

|         |     |   |   |   |   |   |   |   |   |   |   |   |   |   |   |   |   |   |   |   |       |
|---------|-----|---|---|---|---|---|---|---|---|---|---|---|---|---|---|---|---|---|---|---|-------|
| FGF-3   | (81)  | W | S | L | G | A | R | T | G | S | L | Y | C | R | V | G | I | G | F | H | L (100) |
| hstKS3  | (77)  | L | L | G | I | K | R | L | R | L | R | Y | C | N | V | G | I | G | F | H | L (96)  |
| int-2   | (39)  | L | G | G | A | P | R | R | R | K | L | Y | C | A | T | K | - | Y | H | L | - (56)  |
| bFGF    | (23)  | P | G | H | F | K | D | P | K | R | L | Y | C | K | N | G | - | G | F | F | L (41)  |
| aFGF    | (20)  | L | G | N | Y | K | T | P | K | L | L | Y | C | S | N | G | - | G | Y | F | L (38)  |

|         |     |   |   |   |   |   |   |   |   |   |   |   |   |   |   |   |   |   |   |   |       |
|---------|-----|---|---|---|---|---|---|---|---|---|---|---|---|---|---|---|---|---|---|---|-------|
| FGF-3   | (101) | Q | I | Y | P | D | G | K | V | N | G | S | H | E | A | N | M | L | S | V | - (119) |
| hstKS3  | (97)  | Q | A | L | P | D | G | R | I | G | G | A | H | A | D | T | R | D | S | L | - (115) |
| int-2   | (57)  | Q | L | H | P | S | G | R | V | Q | G | S | L | E | N | S | A | Y | S | I | - (75)  |
| bFGF    | (42)  | R | I | H | P | D | G | R | V | D | G | V | R | E | K | S | D | P | H | I | K (61)  |
| aFGF    | (39)  | R | I | L | P | D | G | T | V | D | G | T | K | D | R | S | D | Q | H | I | Q (58)  |

|         |     |   |   |   |   |   |   |   |   |   |   |   |   |   |   |   |   |   |   |   |       |
|---------|-----|---|---|---|---|---|---|---|---|---|---|---|---|---|---|---|---|---|---|---|-------|
| FGF-3   | (120) | L | E | I | F | A | V | S | Q | G | I | V | G | I | R | G | V | F | S | N | K (139) |
| hstKS3  | (116) | L | E | I | L | S | P | V | E | R | G | V | V | S | I | F | G | V | A | R | F (135) |
| int-2   | (76)  | L | E | I | T | A | V | E | V | G | V | V | A | I | K | G | L | F | S | G | R (95)  |
| bFGF    | (62)  | L | Q | L | Q | A | E | E | R | G | V | V | S | I | K | G | V | C | A | N | R (81)  |
| aFGF    | (59)  | L | Q | L | C | A | E | S | I | G | E | V | Y | I | K | S | T | E | T | G | Q (78)  |

FIGURE 6-3

```
        (140)                                           (159)
FGF-3   (136)  F L A M S K G K L H A S A K F T D D C    (155)
hstKS3  (96)   F V A M S S K G K L Y G S P F T D E C    (115)
int-2   (82)   Y L A M N K R G R L Y A S D H Y N A E C  (101)
bFGF    (79)   Y L A M K E D G R L L A S K C V T D E C  (98)
aFGF           F L A M D T D G L L Y G S Q T P N E E C (160)                                           (179)
FGF-3   (156)  K F R E R F Q E M S Y N T Y A S A I H R  (175)
hstKS3  (116)  T F K E I L P N N Y N A Y E S Y K Y P    (135)
int-2   (102)  E F V E R I H E L G Y N T Y A S R L Y R  (121)
bFGF    (99)   F F F E R L E S N N Y N T Y R S R K Y T  (118)
aFGF           L F L E R L E E N H Y N T Y I S K K H A (180)                                           (189)
FGF-3   (176)  T E K T G R E — — — — — — — — — W Y V    (179)
hstKS3  (136)  G — — — — — — — — — — — — — — — M F I    (155)
int-2   (122)  T G S S G P G A Q R P — — — — — W Y V    (125)
bFGF    (119)  S — — — — — — — — — — — — — — — W Y V    (124)
aFGF           E K H — — — — — — — — — — — — — W F V
```

FIGURE 6-4

|  |  | | | | |
|---|---|---|---|---|---|
| FGF-3 (190) | A L N K R G K A K R G C S P R V K P Q H | (209) |
| hstKS3 (180) | A L S K N G K T K K G – – – N R V S P T M | (197) |
| int-2 (156) | S V N G K R P R R G – – – T R R T – Q | (171) |
| bFGF (126) | A L K R T G Q Y K L G – – – S K T G P G Q | (143) |
| aFGF (125) | G L K K N G R S K L G – – – P R T H F G Q | (142) |

| | | |
|---|---|---|
| FGF-3 (210) | I S T H F L P R F K Q S E Q P E L S F T | (229) |
| hstKS3 (198) | K V T H F L P R L * | (206) |
| int-2 (172) | K S L F L P R V L G H K D H E M V R L | (191) |
| bFGF (144) | K A I L F L P M S A K S * | (155) |
| aFGF (143) | K A I L F L P L P V S S D * | (155) |

| | | |
|---|---|---|
| FGF-3 (230) | V T V P E K K N P P S P I K S K I P L S | (249) |
| int-2 (192) | L N S S Q P R A P G E G S Q P R Q K K Q | (211) |

FIGURE 6-5

```
FGF-3   (250) A P R K N T N S V K Y R L K F R F G *  (267)
int-2   (212) S P G D H G K M E T L S T R A T P S T Q  (231)

int-2   (232) L H T G G L A V A *  (240)
```

FIGURE 7D

```
-360             -350            -340           -330
TGGGACCAT    CTGTTCTTGG    CCCTGAGCCG    GGGCAGGAAC
                    DR →

-320             -310            -300           -290
TGCTTACCAC    AGATATCCTG    TTTGGCCCAT    ATTCAGCTGT

-280             -270            -260           -250
TCCATCTGTT    CTTGGCCCCTG   AGCCGGGGCA    GGAACTGCTT
         ← DR | DR →

-240             -230            -220           -210
ACCACAGATA    TCCTGTTTGG    CCCATATTCA    GCTGTTCCAT

-200             -190            -180           -170
CTGTTCCTGA    CCTTGATCTG    AACTTTTCTA    TTCTCAGTTA
    DR →

-160             -150            -140           -130
TGTATTTTTC    CTAGCCCTTGC   AAAATGGCGT    TACCGGAGG
                                              LTR ↓
```

FIGURE 7D (CONTINUED)

```
-120        -110         -100         -90
CTCCCTCCCC  GCACCGGCCA   GTGAGTACAC   AAAGCCGGG

-80         -70          -60          -50
GTGAGGGGAA  GCTTCGCAGG   CGTGCACGGA   GCAGTGAGAT
            Hind III -40         -30          -20          -10         -1
CACTGGGCGTT ATAAATATCC   CGGTGCCAGC   GCGGAGATCC +1          +10          +20          +30         +40
GCTCGGGTGG  CCTCTCTCTT   CCCCTCTCCC   CTTCTCTTCC
                                      ▲

+50         +60          +70          +80
CCGAGGCTAT  GTCCACCCGG   TGCGGCGAGG   CGGGCCAGAG
ORF-1

+90         +100         +110         +120
CAGAGGCACG  CAGCCGCACA   GGGGCTACAG   AGCCCAGAAT
```

ONCOGENE ENCODED POLYPEPTIDE HAVING GROWTH FACTOR ACTIVITY AND METHODS OF USE THEREOF

This application is a continuation-in-part of U.S. Ser. No. 056,137, filed May 29, 1987, the contents of which are hereby incorporated by reference into the subject application.

BACKGROUND OF THE INVENTION

Throughout this application various publications are referenced by numbers within parentheses. Full citations for theses publications may be found at the end of the specification immediately preceding the claims. The disclosures of these publications in their entireties are hereby incorporated by reference into this application in order to more fully describe the state of the art to which this invention pertains.

DNA-mediated gene transfer (DNA transfection) into NIH 3T3 murine fibroblast cells has been a fruitful means for detecting oncogenes in mammalian cellular DNA. The most extensively used transformation assay is the NIH 3T3 focus assay, in which transformed 3T3 cells are detected by their growth into dense foci (1). The focus assay has detected activated oncogenes in the genomes of many tumors and tumor-derived cell lines (2-6). The detected oncogenes are usually members of the ras gene family (5-11), although other genes have been characterized as well (5, 12-15). The alternative oncogene assay monitors tumor formation in immunodeficient mice following injection with transfected NIH 3T3 cells. The oncogenes met (16) and mas (17) were discovered by this method.

This invention discloses the use of a new transformation assay to detect a novel oncogene in DNA from human tumor-derived cell lines. The amino acid sequence encoded by the cDNA of this oncogene shows substantial homology to the previously characterized fibroblast growth factors, bFGF and aFGF (40,41), as well as to the amino acid sequence of two recently characterized oncogenes, int-2 and hst (42,43). For this reason applicants have designated this oncogene FGF-3 and continue this designation in the subject application. However, FGF-3 may alternatively be designated FGF-5 in future publications by the applicants.

SUMMARY OF THE INVENTION

This invention provides a purified polypeptide having growth factor activity and the amino acid sequence shown in FIG. 5 for either ORF-2 or ORF-1. This invention also provides a purified nucleic acid molecule encoding the polypeptides.

This invention further provides a vector which comprises the nucleic acid molecule encoding the polypeptide as well as a host vector system for producing the polypeptide.

This invention also provides a pharmaceutical composition comprising an effective amount of the polypeptide shown in FIG. 5 for ORF-2 and pharmaceutically acceptable carrier. The invention further provides a method of stimulating the proliferation of mesodermal cells, capillary growth and promoting tissue repair by administering an effective amount of the pharmaceutical composi-tion.

This invention also provides a fragment of total human genomic DNA comprising the oncogene designated FGF-3. Additionally, this invention provides a molecule useful as a probe for detecting the oncogene.

This invention still further provides a reagent capable of specifically forming a complex with the polypeptide of this invention and a method for diagnosing a neoplastic condition associated with the presence of an activated oncogene.

BRIEF DESCRIPTION OF THE FIGURES

FIG. 6 (parts 1-5) shows the homology between the predicted FGF-3 protein and other FGF-related proteins. The predicted human FGF-3 amino acid sequence (from ORF-2) is aligned for maximum homology with sequences of the precursor proteins encoded by human hst/KS3, murine int-2, human basic FGF, and human acidic FGF. Amino acid positions of identity or conservative substitution between FGF-3 and related proteins are boxed and shaded. Conservative substitutions are defined as D=E, K=R, S=T, I=L=V, F=Y. Within regions 90-180 and 187-217 of the FGF-3 sequence, there is 50.4% sequence identity with hst/KS3, 47.5% identity with int-2, 43.4% with basic FGF, 40.2% with acidic FGF.

DETAILED DESCRIPTION OF THE INVENTION

Figure 1:
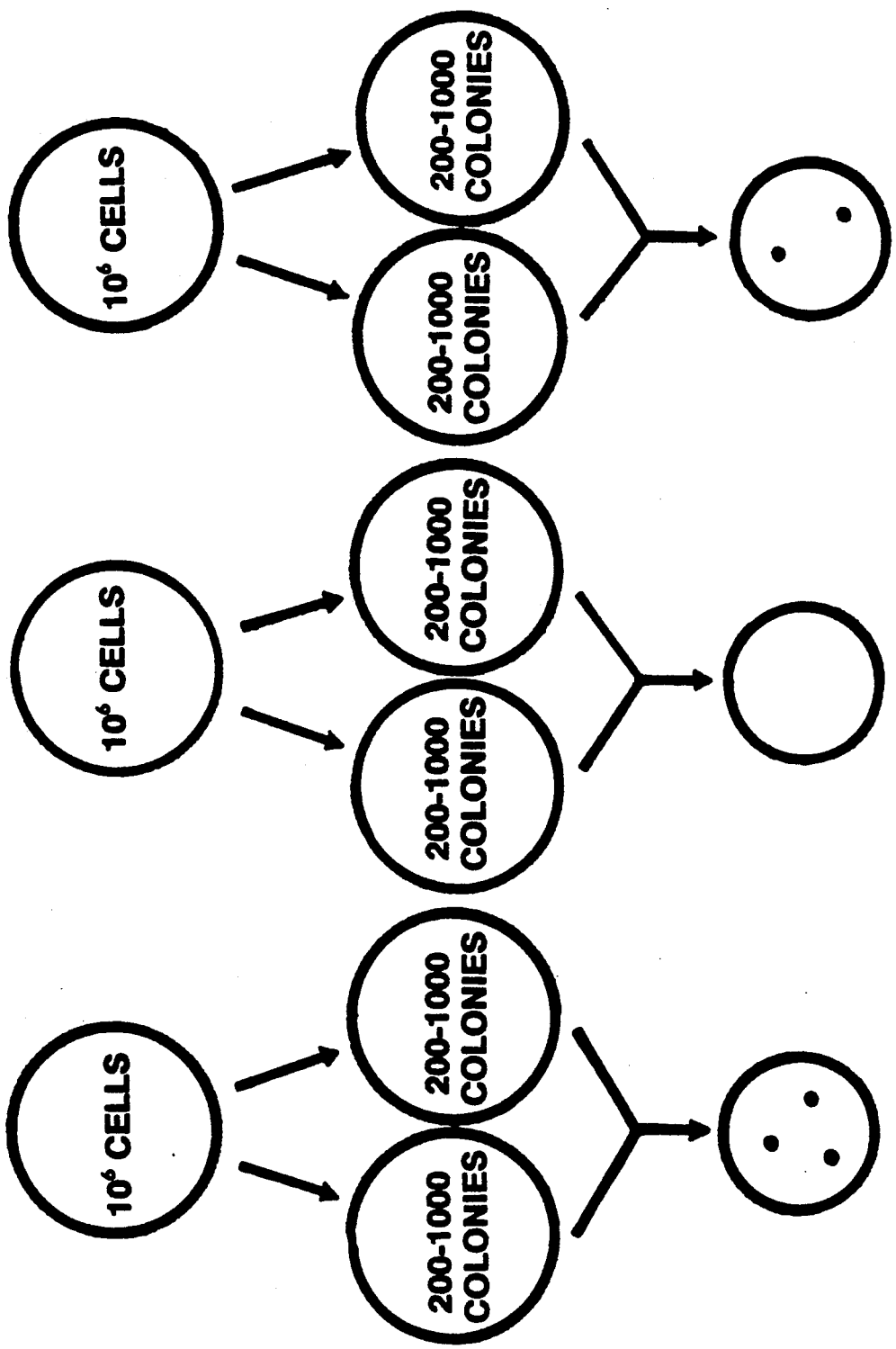
FIG. 1 shows a protocol for detecting oncogenes by defined medium culture. The steps include: 1) Transfect each 100 mm plate with 30 micrograms tumor DNA + 1 microgram pLTRneo. 8 hr. 2) Refeed with DME+-serum.O/N. 3) Trypsinize. Split 1:2. 4) DME+-serum+G418. 12 Days. 5) Trypsinize. 6) Plate $10^5$ cells on fibronectin coated $35^{mm}$ dish. Refeed and maintain in defined medium w/o PDGF/FGF. 7) 8 days.

This invention provides a purified polypeptide having the amino acid sequence shown in FIG. 5 for either open reading frame (ORF) 2 or 1, and a purified nucleic acid molecule encoding the polypeptides. The nucleic acid molecule may be DNA or RNA. Polypeptide analogs having substantially the same amino acid sequence and activity of these polypeptides are also contemplated.

This invention also provides a vector which comprises the nucleic acid molecule of this invention. This vector may be any vector known in the art including a plasmid or a virus. In a perfered embodiment, the plasmid is designated pLTR-122 and is deposited in an *E. coli* strain under ATCC No. 67413.

This invention also provides a host vector system for producing a polypeptide having the amino acid sequence shown in FIG. 5 for ORF-2. The vector comprises a plasmid in a suitable host. The suitable-host may be a eucaryotic cell which in turn may be a mammalian cell. Preferably, the mammalian cell is a NIH 3T3 cell.

This invention further provides a method for producing a polypeptide having the amino acid sequence shown in FIG. 5. The method comprises growing the host vector system of this invention so as to produce the polypeptide in the host and recovering the polypeptide so produced.

This invention still further provides a pharmaceutical composition comprising an effective amount of the polypeptide having the amino acid sequence shown in FIG. 5 and a pharmaceutically acceptable carrier. A method of stimulating the proliferation of mesodermal cells is also provided. This method comprises contacting the mesodermal cells with an effective mesodermal cell proliferating amount of the composition of the pharmaceutical composition. In a perfered embodiment the mesodermal cells are vascular endothelial cells. Additionally, the invention provides a method of stimulating capillary growth comprising contacting the capillaries with an effective capillary stimulating amount of the pharmaceutical composition. Further, a method of promoting tissue repair in a subject with damaged tissue is provided. The method comprises contacting the damaged tissue with an effective tissue repairing amount of the pharmaceutical composition.

This invention also provides a fragment of total human genomic DNA comprising the oncogene designated FGF-3. Additionally, a molecule useful as a probe for detecting the oncogene is provided. This probe may be a polynucleotide or an oligonucleotide.

This invention still further provides a reagent capable of specifically forming a complex with the polypeptide shown in FIG. 5. The reagent is preferably an antibody. The antibody may be a polyclonal antibody or a monoclonal antibody.

A method for diagnosing in a subject a neoplastic condition associated with the presence of an activated oncogene is also provided. The method comprises detecting in the subject the presence of at least a portion of the polypeptide shown in FIG. 5. The subject may be a human being and the detecting may comprise contacting the polypeptide with an antibody which specifically binds to the polypeptide encoded by the activated oncogene to form an antibody-polypeptide complex. The complex so formed is then detected, thereby detecting the presence of the oncogene-encoded polypeptide.

The invention discloses a method of treating cancer in a subject. The method comprises administering to the subject an effective cancer treating amount of the antibody of this invention.

The polypeptide encoded by ORF-1, or a functional equilivant thereof, may be used to influence the translation efficiency of the FGF-3 protein. This influence may either increase or inhibit the translation to the FGF-3 protein.

Materials and Methods

Human Tumor Cell Lines. Tumor cell lines were generously provided by Dr. Jorgen Fogh at the Sloan-Kettering Institute for Cancer Research, Rye, N.Y. Most of these cell lines have been described (19–24). Calu4 was derived from a small cell lung carcinoma by Dr. J. Fogh, and MDA-MB-453 was derived from a breast carcinoma by Dr. R. Cailleau.

Balb/c 3T3 cells, NIH 3T3 cells, and NIH 3T3 cells transformed by various oncogenes were previously described (18, 45). VMCUB2-1 are NIH 3T3 cells transformed with the rearranged, LTR-activated human FGF-3 gene; 3T3-LTR122 are NIH 3T3 cells bearing pLTR122, a plasmid containing 1-2-2 FGF-3 cDNA situated between two MLV LTR elements; 3T3-src and 3T3 ras are NIH 3T3 lines transformed by plasmids bearing the v-src and the mutant human c-H-ras (valine 12) oncogenes. Human tumor cell lines described in several references (19, 20, 21) were obtained from James Loveless at the Memorial Sloan Kettering Cancer Institute; VMCUB1, VMCUB2, 639V, and 253J are from bladder carcinomas, Calu4 and KNS62 from lung carcinomas, BT20, MCF-7 and MDAMB-469 from breast carcinomas, HT29 from a colon carcinoma, SH-1 from a melanoma, SKHEP-1 from a hepatoma, and HEC-1A from and endometrial carcinoma. Fetal bovine heart endothelial cells (FBHE) (46) were obtained from the American Type Tissue Culture Collection.

Preparation of Defined Medium. Defined medium was prepared as described previously (18) by adding supplements to a 3:1 mixture of Dulbecco's medium (DME) and Ham's F12 nutrient mixture, and medium was not used beyond one month after preparation. These supplements were 8 mM NaHC03, 15 mM HEPES pH 7.4, 3 mM histidine, 4 microMolar MnC12, 10 microMolar ethanolamine, 0.1 microMolar selenous acid (sodium salt), 2 microMolar hydrocortisone, 5 micrograms/ml transferrin, 500 micrograms/ml bovine serum albumin/linoleic acid complex, and 20 micrograms/ml insulin. Medium was prepared in autoclaved, water-rinsed glass bottles that had not been exposed to serum nor detergents, and was transferred with sterile plastic pipets. Medium exposed to certain plastic vessels became toxic to cells, and, when necessary, defined medium was stored exclusively in Corning polystyrene tubes or flasks.

DNA Preparation Methods. Mammalian cell DNAs and bacterial plasmid and bacteriophage DNAs were prepared by standard methods (2,25,26).

DNA Transfection and Defined Medium Selection. DNA transfection and selection for transformed clones followed the scheme illustrated in FIG. 1. NIH 3T3 cells were transfected under standard conditions (27) with 30 micrograms cellular DNA and one microgram of plasmid pLTRneo (18) per 100 mm dish, then passaged 1:2 and cultured in DME with serum plus 1 mg/ml G418 for approximately 12 days to select colonies which had acquired pLTRneo and, by cotransfer (27), the transfected cellular DNA. Colonies on each pair of culture dishes were trypsinized and pooled, and 100,000 cells in DME+serum were plated onto poly-D-lysine/fibronectin coated dishes (Nunc) as previously described (18). After cell attachment, cultures were refed with the defined medium described above. Cultures were refed with the same medium the next day and thereafter on a three day schedule until all normal cells died and transformed colonies, if any, had developed (7–10 days). Transformed colonies were individually trypsinized and expanded in DME plus serum. Transformed cultures were freed of any residual normal cells by replating on fibronectin-coated dishes and maintaining in defined medium.

Plasmid Employed for Nucleic Acid Hybridization. Plasmids were provided by Drs. M. Wigler, P. Besmer, F. Alt, R. Axel, and R. Parker. Plasmid clones employed were human H-ras, N-ras, N-myc, rho, murine c-myc, and viral K-ras, mos, src, fos, sis, ski, myb, rel, fps/fes, raf/mil, fms, erbAB, fgr. Blur-2 contains a human Alu repeat sequence (3), which we cloned into the BamHI site of pSP64 (31) to generate pSP6-Alu.

Filter-blotted DNA Hybridization. DNAs were digested with restriction endonucleases, subjected to agarose gel electrophoresis, and transferred to nitrocellulose filters by the method of Southern (32). DNA probes were radiolabelled with 32P by nick translation (33), and 32P-labelled RNA was transcribed from EcoRI-linearized pSP6-Alu DNA using SP6 polymerase (31). Hybridizations with Sp6-derived Alu repeat sequence probes were conducted at 43 degrees C. in the presence of 50% formamide and 10% dextran sulfate (34), while hybridizations with DNA probes were conducted at 70 degrees C. without formamide/dextran sulfate (2).

Filter-blotted RNA Hybridization. Preparations of cytoplasmic RNA (35) were subjected to electrophoresis through formaldehyde agarose gels, transferred to nitrocellulose, and hybridized by standard procedure (34).

Construction and Screening of Genomic DNA and cDNA Libraries in Bacteriophage Lambda. 15 to 20 kilobase pair DNA fragments purified from EcoRI restriction endonuclease digestion of cellular DNAs were ligated to Charon 4A or EMBL3 bacteriophage vectors, packaged into virions, and screened by standard procedure (36, 37). cDNAs were synthesized from polyA+RNA, using RNase and DNA polymerase to synthesize second strands (38). cDNAs were ligated to EcoRI linkers and cloned into bacteriophage Charon 16A.

Tumorigenicity of Transformed Cell Lines. Tumorigencity of transformed cell lines in immunodeficient nude mice followed procedures described elsewhere (39) and outlined in the legend to Table 3.

Construction of Expression Vector. pvcos-7 (obtained from Stephen Goff and Leslie Lobel, Columbia University) is a cosmid with ampicillin resistance, containing a modified Moloney murine leukemia provirus. The provirus has been modified by a deletion of the nucleotide sequence from the Pst1 site (at map position 1.0 kbp) to the Hpa 1 site (at map position 7.6 kbp). An EcoRI linker has been inserted at the cite of the deletion. The pVCOS-7 and the FGF-3 cDNA were both digested with EcoRI. The FGF-3 cDNA was then cloned into the pvcos-7 by standard procedures. The resulting vector was designated pLTR-122. pLTR-122 was then transfected into NIH 3T3 cells by the method described by Wigler et al. (44). The colonies were then trypsinized, pooled and assayed for oncogene transformed cells by a defined medium culture assay (18).

FGF-3 Genomic and cDNA Clones. NIH 3T3 cells transformed by the rearranged FGF-3 gene (the VMCUB2-1 cell line) had been used to clone the FGF-3 gene in lambda vector EMBL4, and these cells were also used to derive the biologically active cDNA clone 1-2-2. An FGF-3 cDNA clone was also obtained by screening a lambda gtll cDNA library derived from RNA of human brain stem (1-day old autopsy) (library kindly provided by Dr. R. Lazzarini). Both cDNAs were subcloned into plasmid pUC8 by EcoRI digestion, which cleaved the cDNAs at a native EcoRI cleavage site 3' to the coding sequences; hence the cDNAs lack their 3' ends and polyA tails. For the purpose of DNA sequencing, fragments of cDNA and genomic clones were subcloned into pUC8 following restriction enzyme digestion or mile DNase I treatment.

DNA Sequencing. Plasmid inserts were sequenced by modification of the standard DNA polymerase dideoxynucleotide chain termination method (47). One to two micrograms plasmid was denatured with alkali, neutralized in the presence of 25 nanograms oligonucleotide primer, and ethanol precipitated. Pellets were dissolved and sequenced with T7 DNA polymerase (Sequenase ®, U.S. Biochemical), using alpha-35S-dATP as the labelled nucleotide. The primers most often used were 17-mers complementary to pUC8 sequences flanking the inserts. The oligonucleotides 5'CCTAAGTGCATCTTGTA-3' and 5'ACTTGCATGGAGTTTTC3', complementary to bases 105-121 and 579-595 of the 1-2-2 FGF-3 cDNA clone, were used in certain experiments. The cDNAs were fully sequenced on both strands, as was the 5' region of the FGF-3 gene. For the purpose of mapping the exon-intron boundaries, certain genomic clones were sequenced on one strand only.

Analysis of FGF-3 RNA. Cytoplasmic RNAs were extracted from cultured cells (35) and in some cases enriched for polyadenylated RNA by oligo-dT cellulose chromatography. RNAs were assayed for FGF-3 transcripts by formaldehyde agarose gel electrophoresis and filter blot hybridization, using standard procedure (34). Ethidium bromide (50 ng/ml) was included in gels to allow visualization of ribosomal RNAs before blotting.

Determination of FGF-3 RNA 5' ends were made by standard primer extension procedure (48). The oligonucleotide 5' CCTAAGTGCAGCTTGTA 3' complementary to bases 105-121 of the 1-2-2 cDNA clone was 5'-end-labelled with gamma-32P-ATP and polynucleotide kinase, and 15 nanograms primer was annealed with ten micrograms polyadenylated cytoplasmic RNAs. The mixture was precipitated, redissolved, incubated with dNTPs and AMV reverse transcriptase (Boehringer Mannheim ®), and analyzed by electrophoresis through a 8M urea-12% polyacrylamide gel followed by autoradiography. DNA sequencing reactions using the same oligonucleotide primer and FGF-3 genomic DNA template were run alongside to provide size markers.

Mitogenic Assays. Transformed NIH 3T3 cells were maintained at high density in a defined medium containing insulin, but lacking platelet-derived growth factor or FGFs (18). After two to three days conditioning, media was harvested for testing of mitogenic activity towards Balb/c 3T3 fibroblasts. To test for activity towards endothelial cells, transformed cells were maintained in DME supplemented with 10 micrograms per ml heparin.

For the fibroblast mitogenic assay, culture wells were seeded to 10% confluence with Balb/c 3T3 murine fibroblasts, and were rendered quiescent by maintaining without refeeding for five days, as originally described (49). Cultures were refed with dilutions of conditioned medium (diluted with defined medium containing insulin), 4 µCi/ml 3H-thymidine was added 15 hours later, and thymidine incorporation into DNA was measured 3 hours later by fixing cultures in 15% trichloroacetic acid, washing with water, dissolving in 0.5M NaOH, and counting by liquid scintillation.

For the endothelial cell mitogenic assay, FBHE endothelial cells were plated at 40,000 cells per 60 mm dish in DME+3% calf serum. The next day, an equal volume of DME+10 µg/ml heparin containing various dilutions of conditioned medium was added, and cell number was determined six days later by trypsinization and counting by hemocytometer.

Heparin Affinity Chromatography. NIH 3T3 cells transformed with the plasmid pLTR122 were used to condition DME medium containing no supplements. Three hundred milliliters of 48 hr. conditioned medium was passed directly through a 1 ml. column of heparin-Sepharose (Pharmacia ®) at room temperature. The column was washed extensively with 0.45M NaCl-20 mM Tris pH 7.5, then washed in succession with tris buffer containing NaCl at 0.6M (3 ml), 0.8M (2 ml), 1.0M (2 ml), 1.5M (2 ml), and 2.0M (2 ml). One ml fractions were collected, and fractions were diluted 1:100 with defined medium containing insulin (18) and assayed for stimulation of Balb/c 3T3 cells.

Results

Defined Medium Transformation Assay. NIH 3T3 cells can grow efficiently in a basal medium supplemented with transferrin, insulin, and fibroblast growth factor (FGF) or platelet-derived growth factor (PDGF), but die in the absence of FGF and PDGF. By contrast, ras-, sis-, src-, and mos-transformed 3T3 cells proliferate in the PDGF/FGF-free defined medium (18). We have developed a transformation assay based upon cell growth in PDGF/FGF-free defined medium (see FIG. 1 and Methods). Cultures of 3T3 cells are transfected with cellular DNA and pLTRneo, selected with neomycin analog G418 to enrich for cells with stably acquired foreign DNA, and then selected in PDGF/FGF-free defined medium.

We have performed transfections with DNAs from seventeen human tumor-derived cell lines, and have used human placental and NIH 3T3 DNAs as negative controls. The results are tabulated in Table 1.

DNAs generated secondary transformants upon transfection.

TABLE 2

Selection of Transformed Cells Following Transfection of NIH 3T3 Cells with DNAs from Primary Transformant Cell Lines

| Primary Transformant Cell Line | #G418r Colonies Screened | Number of Secondary Transformants | Transformants per 10,000 G418r Colonies |
|---|---|---|---|
| SAOS2-2 | 16,000 | 0 | 1 |
| SAOS2-3 | 5,000 | 2 | 4.0 |
| VMCUB2-1 | 6,500 | 3 | 4.7 |
| VMCUB2-2 | 13,000 | 4 | 3.1 |
| SKNMC-1 | 3,000 | 3 | 10.0 |
| SKNMC-2 | 6,500 | 3 | 4.7 |
| SKNMC-3 | 9,500 | 0 | 1 |
| SKMES-1 | 6,000 | 1 | 1.7 |
| SMKES-2 | 7,000 | 4 | 5.7 |
| SKMES-3 | 8,500 | 3 | 3.6 |

Table 2. Primary transformant cell lines derived from transfection and defined medium selection as listed in Table 1. E.g., VMCUB2-2 derived from transfection

TABLE 1

Selection of Transformed Cells Following Transfection if NIH 3T3 Cells with NDAs from Human Tumor Cell Lines

| Tumor Cell Line | Tissue of Origin | #G418r Colonies Screened | Number of Independent Transformants | Transformants per 10,000 G418r Colonies | Ras Homology |
|---|---|---|---|---|---|
| Calu-4 | Lung | 8,000 | 8 | 10 | K-ras |
| KNS 62 | Lung | 9,500 | 4 | 4.1 | H-ras |
| SAOS-2 | Bone | 15,000 | 4 | 2.7 | None |
| 639 V | Bladder | 15,000 | 2 | 1.3 | K-ras |
| Sk-N-MC | Neural | 29,000 | 4 | 1.3 | None |
| VM-CUB-2 | Bladder | 19,000 | 2 | 1.1 | None |
| SK-MES-1 | Lung | 53,000 | 4 | 0.8 | None |
| SW 1088 | Astrocyte | 22,000 | 1 | 0.5 | None |
| A 172 | Neural | 9,000 | 0 | | |
| BT-20 | Breast | 9,000 | 0 | | |
| HT 1376 | Bladder | 8,000 | 0 | | |
| 5637 | Bladder | 6,500 | 0 | | |
| MCF-7 | Breast | 8,000 | 0 | | |
| SK-HEP-1 | Liver | 7,000· | 0 | | |
| VM-CUB-1 | Bladder | 6,500 | 0 | | |
| IMR-32 | Neural | 9,000 | 0 | | |
| MDA-MB-453 | Breast | 8,000 | 0 | | |
| Nontransformed Cells | | | | | |
| NIH 3T3 | | 95,000 | 0 | 0.1 | |
| Human placenta | | 84,000 | 1 | 0.1 | |

Table 1. NIH 3T3 cells transfected with tumor cell DNA and pLRneo were first selected for G418 resistance in serum-containing medium. The number of G418r colonies were approximated prior to pooling and culturing in PDGF/FGF-free defined medium. Transformed colonies were considered to derive from independent transfection events if they arose on separate defined media dishes. Transformant containing human ras oncogenes are indicated.

DNAs from eight of the tumor cell lines gave transformants upon transfection, with frequencies ranging from greater than ten transformants per 10,000 G418-resistant colonies screened for Calu-4 lung carcinoma DNA to 0.5/10,000 for SW1088 astrocytoma DNA. Transfections with normal human and mouse DNAs have yielded one transformant for 179,000 G418-resistant colonies screened.

DNA was prepared from transformants derived by transfection with human tumor cell line DNAs. These transformant DNAs were used in a second cycle of 3T3 cell transfection, G418 selection, and defined medium selection. As shown in Table 2, most transformant with DNA from human tumor cell line VMCUB2. Transfection and selection procedures were as described in Table 1.

In some instances, DNAs from secondary transformants were transfected into 3T3 cells to generate tertiary transformants (data not shown).

Tumorigenicity of Transformed Cell Lines. Seven transformed cell lines which derived from transfection with DNAs from four human tumor cell lines were tested for tumorigenicity. Trypsinized cell suspensions were inoculated into athymic nu/nu (nude) mice, which were monitored for tumor development. As shown in Table 3, six of the seven transformed cell lines were strongly tumorigenic, inducing progressive tumors in all inoculated mice within two weeks.

TABLE 3

Tumorigenicity of Transformed Cell Lines in Nude Mice

| Transformant Inoculated | No. Mice with Tumors/ No. Mice Inoculated | Latency (weeks) |
|---|---|---|
| SAOS2-3-1 | 3/3 | 2 |
| SAOS2-3-1-1 | 3/3 | 1-2 |

TABLE 3-continued

Tumorigenicity of Transformed Cell Lines in Nude Mice

| Transformant Inoculated | No. Mice with Tumors/ No. Mice Inoculated | Latency (weeks) |
|---|---|---|
| VMCUB2-1-1 | 3/3 | 1-2 |
| VMCUB2-1-2 | 1/3 | 6 |
| SKMES-4 | 3/3 | 1-2 |
| SKMES-5 | 3/3 | 1-2 |
| SKNMC-3 | 3/3 | 1-2 |
| NIH 3T3 | 0/3 | No tumors after 11 weeks |

Table 3. Transformed cell lines and normal NIH 3T3 cells were trypsinized, counted, and inoculated subcutaneously into athymic nu/nu mice, as previously described (54). Two million cells were injected per mouse, except for cell lines VMCUB2-1-2 and SKMES-4, for which one million cells were used. Mice were monitored weekly for appearance and progression of tumors at site of inoculation. The latency period is the average period for appearance of progressive tumors.

The seventh transformant was weakly tumorigenic, while normal NIH 3T3 cells were not tumorigenic over the eleven week monitoring period. Hence, the transfected genes which confer growth factor independence also confer oncogenic potential to 3T3 cells.

Figure 2:
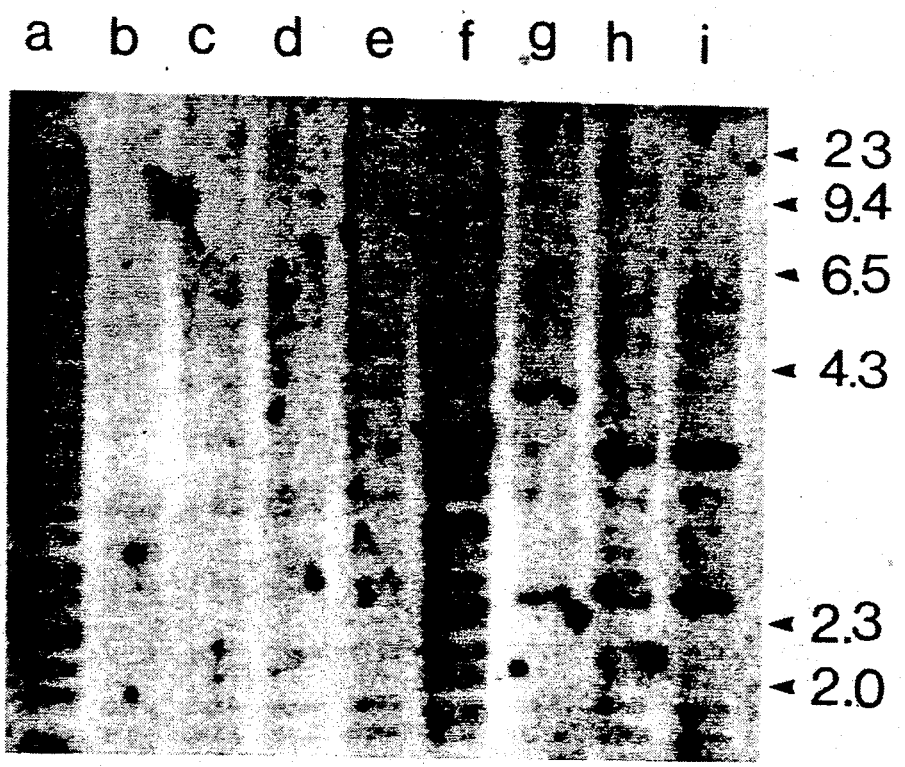
FIG. 2 shows human Alu repeat sequences in transformants derived from VMCUB2 tumor DNA transfections. EcoRI-digested DNAs from primary and secondary transformants of VMCUB2 were analyzed by filter blot hybridization with pSP6-Alu 32P-RNA. DNA from primary transformant VMCUB2-2 (lane a) and its secondary transformants (b-e), primary transformant VMCUB2-1 (f) and its secondary transformants (g-i). Arrows denote size markers (in kbp).

Structure of the Oncogene in a Transformant Derived by Transfection with VMCUB2 Bladder Carcinoma DNA. Four secondary transformants derived from primary transformant VMCUB2-2 lack Alu repeats (FIG. 2, lanes b-e) while three transformants derived from primary VMCUB2-1 each have two Alu sequences (lanes g-i), one of which is within a conserved 2.3 kbp EcoRI DNA fragment. Hence, different molecular events gave rise to the two primary VMCUB2 transformants. The human oncogene in transformant VMCUB2-1 has been cloned from a phage genomic library of secondary transformant VMCUB2-1-1. Initial clones were obtained by Alu sequence homology, and further clones were obtained by genomic walking.

Figure 3:
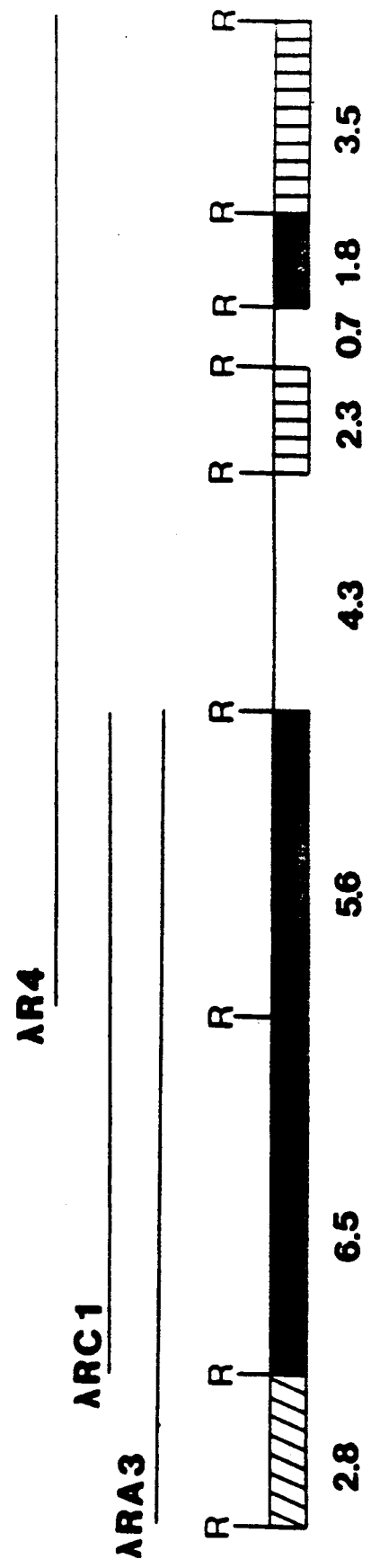
FIG. 3 shows the physical map of the FGF-3 oncogene. The inserts of three overlapping genomic clones are shown. Kilobase pair lengths (in kbp) of EcoRI (R) restriction fragments are indicated. Fragments containing Alu repeats are indicated with vertical hashmarks, fragments homologous to the oncogene cDNA clone are indicated as solid boxes, and the 2.8 kbp fragment derived from pLTRneo is marked with diagonal stripes.

A physical map of the FGF-3 oncogene is shown in FIG. 3. The genomic inserts in the RA3 and R4 phage DNA isolated lack transforming activity. However, a ligated mixture of RA3 and R4 partial EcoRI digests gave many transformed colonies following transfection (data not shown). This demonstrates that these two overlapping clones span the entire oncogene. As shown in FIG. 3, three genomic EcoRI fragments in the gene hybridize to a 1.1 kbp cDNA corresponding to the transcript of this gene. This cDNA was transforming activity when fused to a retroviral promoter. We have hybridized this cDNA clone at low stringency to a panel of eighteen known oncogenes and have failed to detect sequence homology.

The coding strand of the cDNA was determined by sequencing the long open reading frame (see below), and the 5'-3' orientation of the genomic DNA map was determined by mapping genomic restriction enzyme sites corresponding to sites on the cDNA.

Surprisingly, we found that the 2.8 kbp EcoRI fragment at the 5' end of the oncogene locus hybridized to the identically sized RI fragment of pLTRneo (FIG. 3). Further mapping of restriction sites at the 5' end of the oncogene allowed us to conclude that transfection of VMCUB2 bladder carcinoma DNA together with pLTRneo had resulted in a fortuitous DNA rearrangement, whereby the LTRneo plasmid became linked to the 5' end of the oncogene in a 5'-5' orientation. The breakpoint between human and plasmid DNAs is located within the 1 kbp region between the XbaI site in LTRneo and the PstI site in the 5' transcribed region of the human gene.

Figure 4:
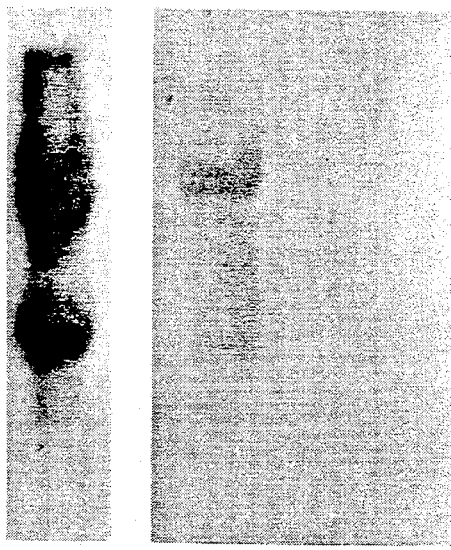
FIG. 4 shows the hybridization of RNAs to the FGF-3 oncogene cDNA probe. Cytoplasmic RNAs (10 micrograms) from secondary transformant VMCUB2-1-1 (lane a), human tumor cell line VMCUB2 (b) and NIH 3T3 cells (c) were analyzed by formaldehyde-agarose gel electrophoresis transfer to nitrocellulose, and hybridization to the 32P-labelled VMCUB2-1 oncogene cDNA. The autoradiogram was exposed 3 hrs (lane a) and 24 hr (lanes b, c). Migration of 18S and 28S rRNAs are indicated.

This rearrangement probably results in increased oncogene expression due to the influence of the retrovirus enhancer element in pLTRneo. This is supported by RNA filter blot analysis, using the oncogene cDNA as hybridization probe. As shown in FIG. 4, the cDNA detects two abundant transcripts (@18S and @28S) in a transformant bearing the FGF-3 oncogene (lane a). This expression is dramatically higher (approximately 50-fold) than that seen in the human bladder carcinoma cell line VMCUB2 (lane b). The sizes of transcripts in the human and transformed cells are approximately the same, suggesting that LTR-enhanced transcription proceeds from the native human promoter(s).

RNA Transcribed from the Rearranged Oncogene Encodes a Protein Related to Fibroblast Growth Factors. One oncogene cDNA (clone 1-2-2) of 1121 base pairs has been completely sequenced and is presented in FIG. 5. The 1120 base pair sequence lacks the 3' polyA tract, because the cDNA cloning procedure involved EcoRI digestion which cut the native cDNA at least once. The single strand shown corresponds to that of the RNA, as demonstrated by the ability of an oligonucleotide of complementary sequence to prime reverse transcription of the oncogene-encoded RNA (see below). The cDNA sequence contains two ATG-initiated open reading frames (ORFs); ORF-1 and ORF-2 can specify polypeptides of 38 and 267 amino acid residues, respectively. The two reading frames slightly overlap, with the ORF-1 termination codon, TGA, situated one nucleotide downstream of the ORF-2 initiator ATG.

The protein specified by ORF-2 bears a leucine-rich hydrophobic amino terminus, which may serve as a signal sequence for cotranslational transport into the endoplasmic reticulum (53). The protein's lack of other extensive tracts of hydrophobic residues suggests that the ORF-2 product can be secreted. The predicted protein also bears a consensus sequence for N-linked glycosylation, AsnGlySer (109-111). When the ORF-2 protein sequence was compared with sequences in the PIR-NBRF (Protein Identification Resource, National Biomedical Research Foundation) database, substantial homology was detected between the ORF-2 protein and both acidic and basic fibroblast growth factors. The recently described int-2 and hst/KS3 predicted protein sequences are also homologous to, but distinct from, the ORF-2 protein, which we here term FGF-3.

A comparison of the FGF-3 amino acid sequence with those for other FGF family proteins is shown in FIG. 6. Two blocks of FGF-3 amino acid residues (90-180, 187-207) show substantial homology to the other proteins, ranging from 40.2% (versus acidic FGF) to 50.4% (versus hst/KS3). Within these homology blocks, the five proteins are identical at 20% of the residues, and allowing for conservative amino acid substitutions, the five proteins share 29% homology. Nucleotide sequence homology between the FGF-3 coding sequences and those of the related genes is minimal.

The sequences of the FGF-related proteins differ in several respects. First, the five sequences differ in the length and sequence of residues between the two homology blocks and distil to them. Second, the FGF-3 sequence is unique in bearing an insertion within the second homology block (CysSer, 201–202). Lastly, the amino-terminal sequences of the FGF-3, hst/KS3, and int-2 proteins are extensively hydrophobic, while those of acidic and basic FGF precursor proteins are not, suggesting differences in post-translational trafficking amongst the FGF-like proteins.

The Structure of the FGF-3 Oncogene is Similar to Those of Other FGF-Related Genes. The structure of the rearranged, transforming FGF-3 oncogene is illustrated in FIG. 7, Panel A. The portion of the oncogene's transcripts represented in the transforming cDNA clone 1-2-2 derive from three exons in the gene. The DNA sequences at the exon-intron boundaries and their positions with respect to the coding sequence are presented in panel B of FIG. 7. Exon I spans coding sequences from the initial codon through the first nucleotide of serine codon 118, while exon II terminates after serine codon 152. Since the splice boundaries are at points within the FGF family homology blocks, we could compare these exon boundaries to those within the hst/KS3, int-3, and basic FGF genes (54, 55, 56). The exon boundaries of both the hst/KS3 and int-2 oncogenes are positioned identically to those of the FGF-3 gene. The exon II/III boundary of the basic FGF gene also aligns perfectly, while the exon I/II boundary of this gene is shifted by three nucleotides. Hence, the FGF-related genes have evolved with virtually no deviation from their ancestral gene's exon structure. The FGF-related genes bear introns of dramatically different lengths: hst/KS3 introns total 1.1 kbp, FGF-3 introns total 19 kbp, and basic FGF gene introns exceed 30 kbp.

Figure 5B:
FIG. 5 (parts A-C, part C contains subparts 1-4) shows structures and sequence of FGF-3 cDNA clones. A) The structure of the 1-2-2 cDNA clone corresponding to a transcript of a rearranged, activated human oncogene. Several restriction endonuclease cleavage sites are indicated: E=EcoRI, B=BamHI, S=SmaI, P=PstI. B) Structure of a homologous cDNA clone isolated from a library of human brain stem RNA (one day old, autopsy). The library was kindly provided by Dr. R. Lazzarini. The circled EcoRI sites at the left ends of both cDNAs are part of synthetic linker sequences added during cloning. C) Sequence of the 1-2-2 cDNA clone depicted in panel A. The nucleotide sequence (1120 bases) is shown along with the predicted amino acid sequences specified by the two open reading frames, ORF-1 and ORF-2. The homologous brain cDNA sequence is identical to bases 246–1120 depicted here.
Figure 7A:
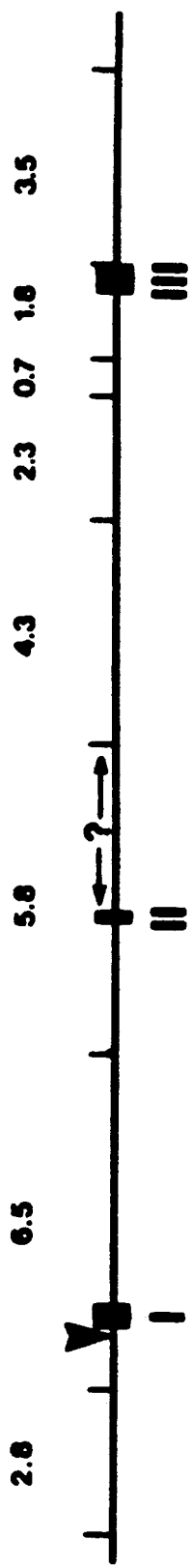
FIG. 7 (parts A-D) shows the structure of the rearranged, activated FGF-3 oncogene. A) Structural map of the rearranged FGF-3 gene. Thin hashmarks indicate positions of EcoRI cleavage sites, and the sizes of the EcoRI fragments (in kilobase pairs) are indicated above the map. The three exons are denoted by solid boxes marked I, II, and III. The precise locations of exons I and III were obtained by mapping restriction sites in the genomic DNA which correspond to sites in the cDNA clone. Exon II lies within the 5.8 kbp EcoRI fragment, but its precise positon was not determined (signified by the "?" symbol). The arrowhead marks the point of rearrangement between the native FGF-3 gene and plasmid pLTRneo. B) Sequences at the exon-intron boundaries. Exon sequnces are shown in capital letters, intron sequences in small case. Only sequences near the boundaries are shown. Exon sequences are numbered according to the corresponding FGF-3 1-2-2 cDNA clone sequence (FIG. 1C). The corresponding amino acid sequence of FGF-3 is shown above exon sequences. C) Schematic diagram illustrating the rearrangement between the native FGF-3 gene and plasmid pLTRneo which generated the activated FGF-3 gene. Solid box indicates exon I of FGF-3 gene, rightward arrows marking site of FGF-3 transcription initiation. One of the two LTR sequences in pLTRneo is shown in open box, with its promoter initiating transcription from the leftward arrow. Diagonally shaded areas within LTR are the 75 base pair repeats which contain the enhancer. Vertical arrowheads mark breakpoints in pLTRneo and native FGF-3 gene accompanying rearrangement. E=EcoRI site, H=HindIII site. D) Sequence of rearranged FGF-3 gene in the promoter region. The sequences are numbered corresponding to the site of transcription initiation (+1), mapped by primer extension analysis. The arrow at +23 corresponds to the first base in the 1-2-2 cDNA clone (FIG. 1C). A TATAA box presumptive promoter element (−31 to −27) is bracketed. LTR sequences in the rearranged gene lie upstream from −129. The direct repeat elements of the LTR are marked "DR".
Figure 7A:
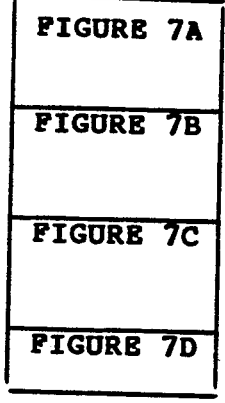
Figure 7B:
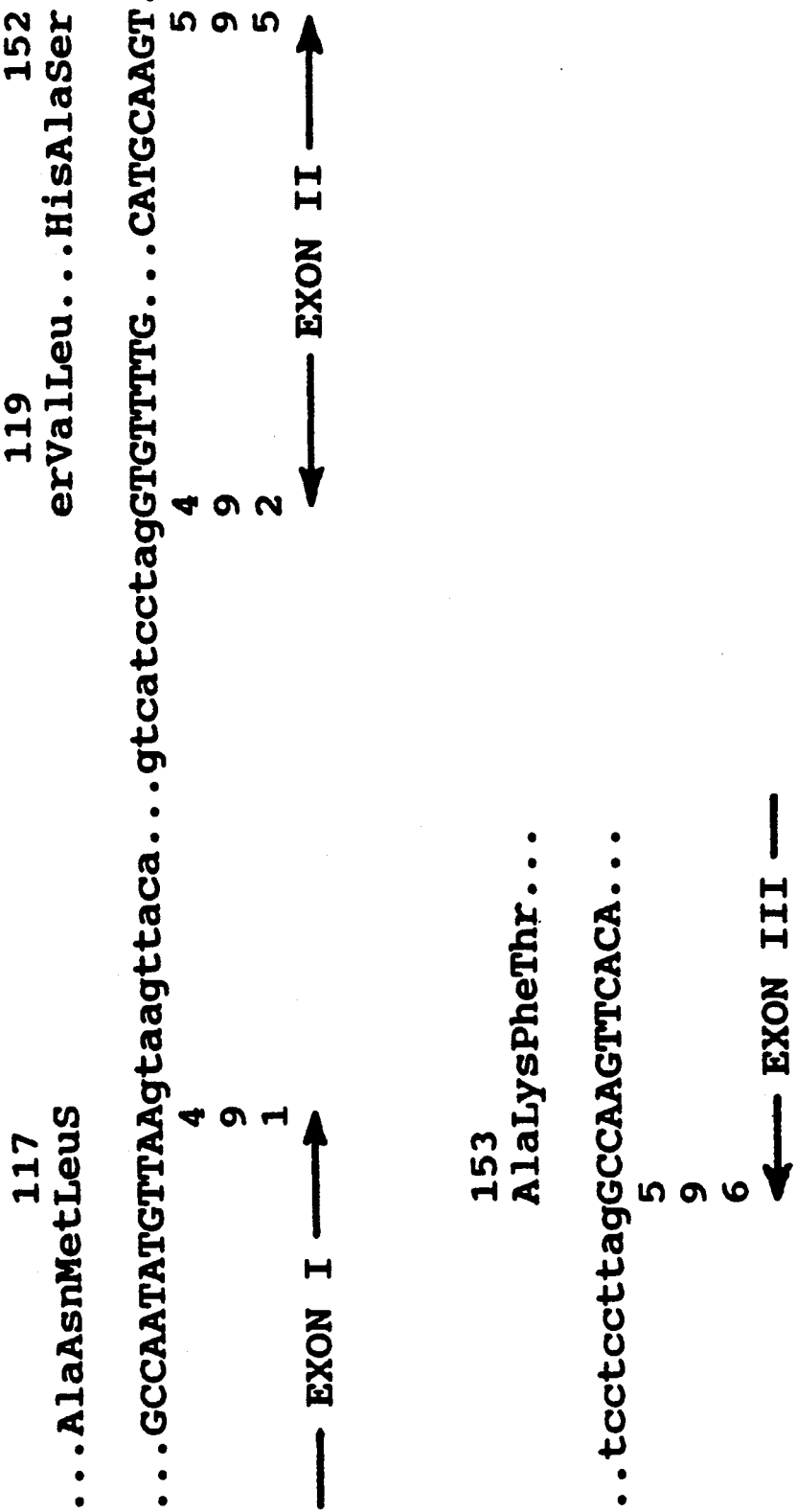
Figure 7C:
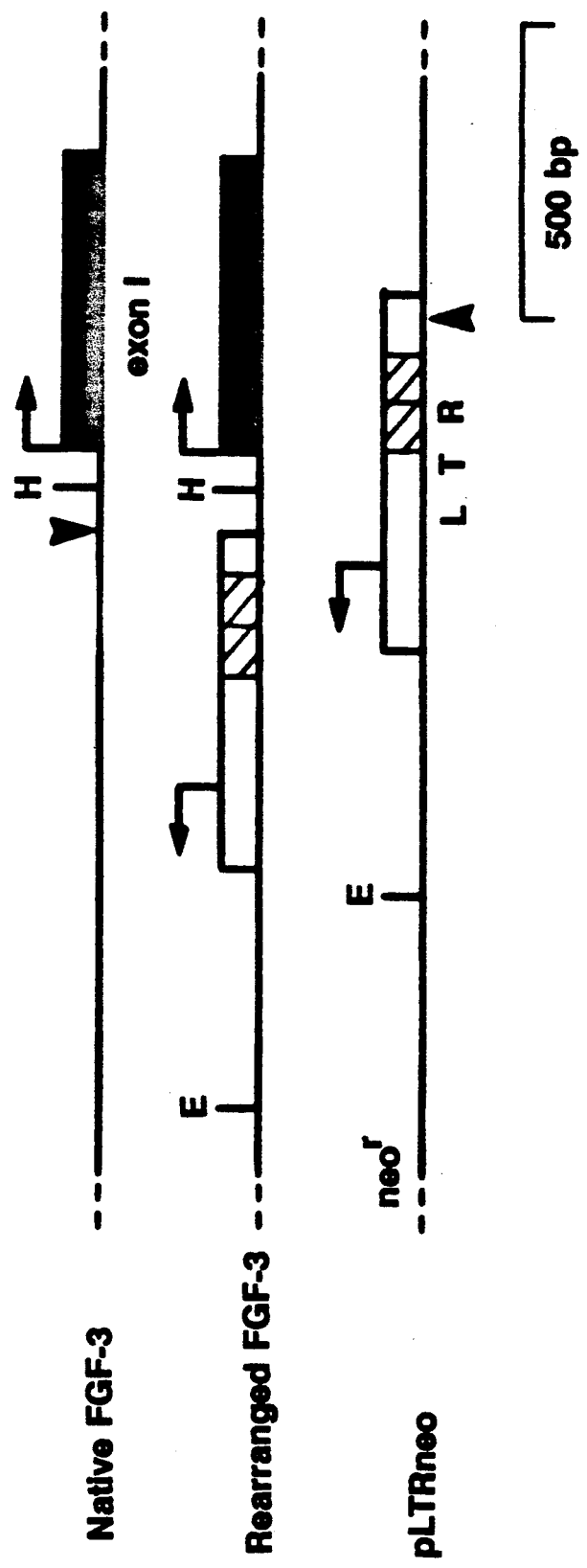

Expression of the Native FGF-3 Gene. We have examined whether the native FGF-3 gene specifies the same RNA transcripts and protein as does the rearranged, LTR-activated gene. One approach we have used has been to characterize cDNA clones corresponding to transcripts of the native FGF-3 gene. Based upon preliminary data suggesting expression of FGF-3 in fetal brain, we chose to screen a cDNA library constructed in lambda gt11 vector using RNA from autopsy of one-day old human brain stem (library kindly provided by Dr. R. Lazzarini). Four clones hybridizing to the FGF-3 gene were detected upon library screening, one of which was subcloned and fully sequenced. This brain cDNA clone was 245 nucleotides shorter than the 1-2-2 FGF-3 cDNA clone (FIG. 5B), but the sequence of the brain cDNA was identical to that of bases 246 to 1120 in the 1-2-2 clone's sequence (FIG. 5C).

Figure 9:
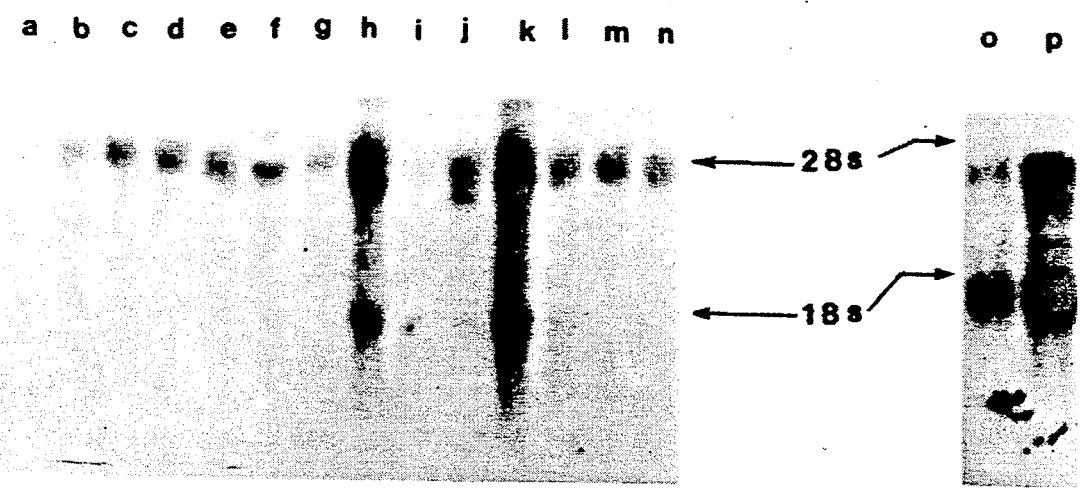
FIG. 9 shows northern blot analysis of FGF-3 RNA in human tumor cell lines. Ten micrograms of total cytoplasmic RNAs (lanes a-n) or one microgram polyA-selected cytoplasmic RNAs (lanes o, p) were subjected to electrophoresis through 1.5% agarose gels containing 2.2M formaldehyde. Gel-embedded RNA was transferred to nitrocellulose, hybridized with nick-translated FGF-3 1-2-2 cDNA, and autoradiographed. Total RNA from NIH 3T3 cells (lane a), human tumor cell lines VMCUB1 (b), VMCUB2 (c), Calu4 (d), KNS62 (e), BT20 (f), MDAMB469 (g), SKHEP-1 (h), MCF-7 (i), HEC-1A (j), 639V (k), 253J (l), HT29 (m), SH1 (n). PolyA RNA from 639V (o) and from NIH 3T3 transformant VMCUB2-1 bearing the rearranged, LTR-activated FGF-3 gene (p). The positions of 18S (1.9 kb) and 28S (4.5 kb) ribosomal RNAs are indicated.

We have also loked for expression of FGF-3 within a panel of human tumor cell lines of solid tumor origin. Cytoplasmic RNAs were prepared from thirteen such cell lines, and the samples were assayed for FGF-3 transcripts by gel electrophoresis and filter blot hybridizaiton. None of htese cell lines had shown any evidence for FGF-3 gene rearrangement (data not shown). FIG. 9 shows that two of the cell lines, hepatoma SKHEP1 and bladder carcinoma 639V, express two RNA species homologous to the FGF-3 cDNA probe (lanes h,k). A third cell line, endometrial carcinoma HEC-1A, expressed FGF-3 RNA at lower levels (lane j), while the other tumor cell lines did not express FGF-3 detectably. (The cDNA probe also hybridized weakly to human 28S ribosomal RNA.)

Figure 8:
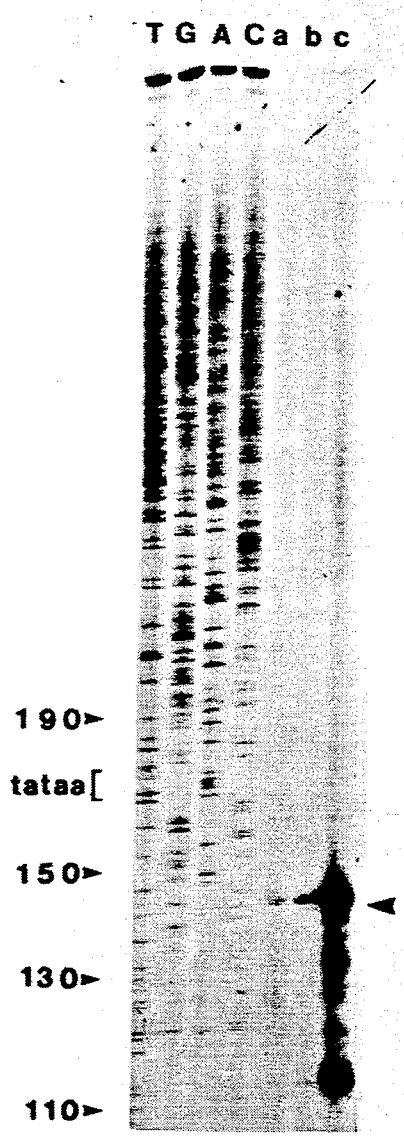
FIG. 8 shows mapping the 5' end of FGF-3 RNAs by primer extension analysis. Ten micrograms total cytoplasmic RNAs were annealed with the oligonucleotide 5' (32P) PO4-CCTAAGTGCATCTTGTA-3'OH complementary to FGF-3 RNA (bases 105-121 of 1-2-2 cDNA clone), and the mixture was incubated in buffer containing deoxynucleoside triphosphates and AMV reverse transcriptase. Reaction products were resolved on a 8M urea-12% polyacrylamide sequencing gel. RNAs from human tumor cell lines 639V (lane a) and SKHEP-1 (lane b) and from 3T3 transformant VMCUB2-1 (lane c) were used as templates. The same oligonucleotide (but unlabelled) was used to prime DNA sequencing reactions, using a subclone of the rearranged FGF-3 gene as template. Sequencing reactions are designated A, C, G, T corresponding to the sense strand of the FGF-3 gene, and lengths along the sequence ladder are numbered alongside the figure. A TATAA box upstream of the transcribed sequences is indicated.

The FGF-3 transcripts in the tumor cell lines were indistinguishable in size and relative abundance from the two RNA species transcribed from the rearranged, LTR-activated FGF-3 gene in transformed 3T3 cells (FIG. 9, lanes o, p). By primer extension analysis, we could show that at least one of the native FGF-3 transcripts in SKHEP1 and 639V cells has precisely the same 5' end as that which was characterized for a transcript of the rearranged gene (FIG. 8, lanes a, b). Taken together, these data confirm that RNA species encoded by native and rearranged FGF-3 genes are the same.

FGF-3 Transformed 3T3 Cells Secrete a Mitogen Functionally Related to FGFs. Our sequence data suggests that the FGF-3 gene encodes a secreted growth factor. We have linked the FGF-3 cDNA clone to the mammalian expression plasmid vector pvcos-7. This construct, termed pLTR-122, transforms fibroblasts with high efficiency. pLTR-122 has been transfected into NIH 3T3 cells to derive transformants which express the oncogene and secrete the FGF-3 encoded growth factor.

We have assayed for mitogenic activity secreted from 3T3 cells transformed by the rearranged FGF-3 gene or by FGF-3 cDNA linked to MLV-LTR sequences. Conditioned media from such transformed cell cultures (termed VMCUB2-1 and 3T3-LTR122, respectively) were serially diluted and assayed for the ability to stimulate DNA synthesis in quiescent Balb/c 3T3 fibroblast cultures. Table 4 shows that these transformed cells secrete mitogenic activity detectable at 1:8 dilutions. Secretion of mitogenic activity is not a property of transformed cells per se, as NIH 3T3 cells transformed by activated human H-ras or viral src oncogenes released little or no mitogenic activity (Table 4).

TABLE 4

| Stimulation of Quiescent Balb/c 3T3 Cells with Conditioned Media | | |
|---|---|---|
| Conditioned Medium From | Dilution | 3H-Thymidine Incorporation (cpm/10,000 |
| 3T3-ras | 1:2 | 1.1 |
|  | 1:4 | 1.5 |
|  | 1:8 | 1.0 |
| 3T3-src | 1:2 | 1.5 |
|  | 1:4 | 1.1 |
|  | 1:8 | 1.1 |
| VMCUB2-1 | 1:2 | 23.0 |
|  | 1:4 | 9.5 |
|  | 1:8 | 3.2 |
| 3T3-LTR122 | 1:2 | 130.0 |
|  | 1:4 | 99.1 |
|  | 1:8 | 40.8 |
| No conditioned medium | | 0.9 |
| with 10% calf serum | | 146.0 |

Balb/c 3T3 cells were plated in culture wells (20,000 cells/ 2.0 sq. cm. well) in serum-containing medium and maintained five days without refeeding, allowing the cells to form quiescent, serum-exhausted monolayers. Cultures were refed with serum-free medium containing dilutions of conditioned medium from transformed cells. 3H-thymidine (4 $\mu$Ci/ml) was added 15 hrs. later, and after three hour incubation, cultures were fixed in 15% trichloroacetic acid, their DNA dissolved in 0.5N NaOH, and incorporated label was assayed by liquid scintillation.

Figure 10:
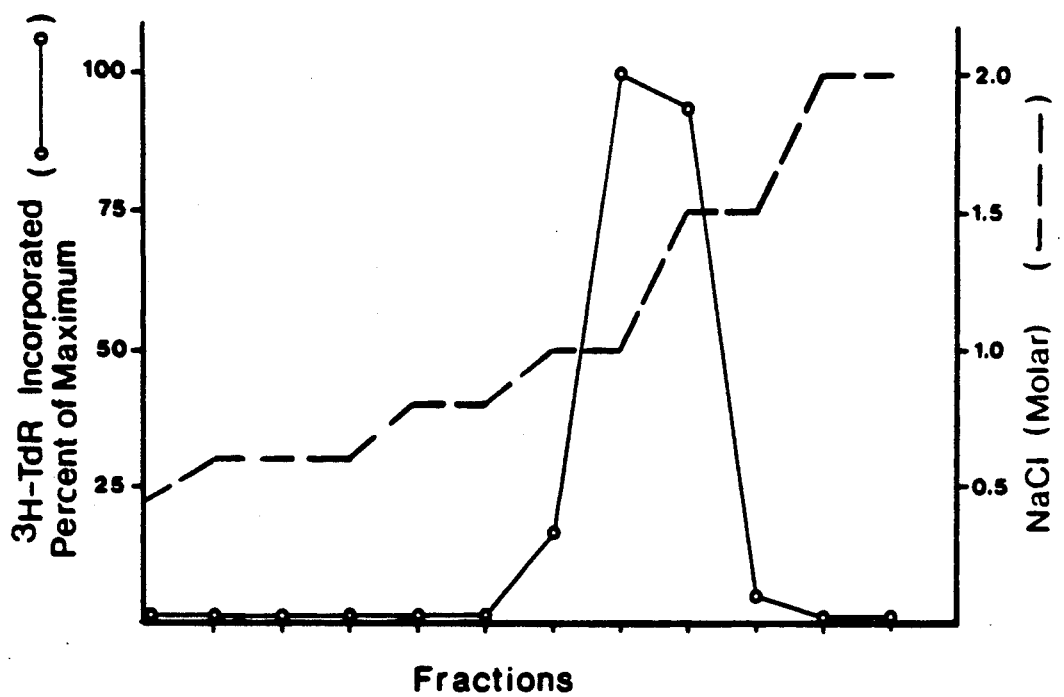
FIG. 10 shows Heparin Sepharose chromatography of mitogenic activity secreted from transformed cells expressing FGF-3. NIH 3T3 cells transformed by plasmid pLTR122 (containing FGF-3 cDNA linked to LTR sequences) were used to condition 300 ml of serum-free medium. Conditioned medium was passed over a 1.0 ml Heparin-Sepharose column at room temperature, and the column was washed with 20 ml Tris (ph 7.5) buffer containing 0.45M NaCl. Bound material was eluted stepwise with Tris-buffered NaCl solutions (0.6, 0.8, 1.0, and 2.0M). Ten microliters of the 1 ml fractions were assayed for ability to stimulate DNA synthesis in quiescent Balb/c 3T3 cell cultures. Tritiated thymidine incorporation data is expressed as percentage of maximum incorporation attainable in the assay using 10% calf serum (1.5×106 cpm per 100,000 cells).

As a means of assessing whether the mitogen secreted by FGF-3 transformed cells is, indeed, FGF-3, we have tested whether this mitogen has properties diagnostic for FGFs. One property of acidic and basic FGFs is their ability to strongly bind to the glycosaminoglycan heparin (50, 51, 52). Elution of FGFs from heparin affinity resins requires NaCl concentrations of 1.0M or greater. By contrast, platelet-derived growth factor, a basic protein which binds heparin by weaker ionic interactions, elutes at approximately 0.5M NaCl. Mitogenic conditioned medium from FGF-3 cDNA-transformed 3T3 cells was passed directly over a heparin-Sepharose column, which was washed extensively with buffered 0.45M NaCl, and then eluted with stepwise increasing salt concentrations. Dilutions of column fractions were assayed for the ability to stimulate quiescent Balb/c 3T3 cells. As shown in FIG. 10, the peak of mitogenic activity eluted in the 1.0 and 1.5M NaCl fractions.

A second property of FGFs is their broad spectrum of mitogenicity, including their activity towards vascular endothelial cells. Conditioned medium from FGF-3 transformed cells was tested for ability to stimulate proliferation of bovine heart endothelial cells. Table 5 shows that the conditioned medium stimulated endothelial cell growth as effectively as could partially purified basic FGF. These data strongly suggest functional similarity between FGF-3 and the well characterized fibroblast growth factors.

TABLE 5

Factor Released from FGF-3 Transformed Cells Stimulates Endothelial Cell Growth

| Culture Medium Supplement | Number of Cell Doublings |
|---|---|
| None | 1.5 |
| 50 ng/ml FGF | 3.1 |
| Conditioned medium from 3T3-LTR122 cells | |
| 1:2 dilution | 3.3 |
| 1:8 dilution | 3.4 |

Fetal bovine heart endothelial cells (FBHE) were plated onto 60 mm tissue culture dishes (40,000 cells per dish) using DME medium containing 3% calf serum. After 24 hours, two plates of cells were individually trypsinized, and cell numbers determined by hemocytometer (60,000 cells +/−10%). The media on other plates was diluted with an equal volume of DME+10 micrograms/ml heparin+test substance. Cultures were maintained without refeeding for six days, and cell counts were determined by hemocytometer after trypsinization. Test substances were either crude FGF (Collaborative Research) (50 ng/ml final concentration) or dilutions of medium conditioned by the 3T3-LTR122 FGF-3 transformed cell line. Growth is expressed as number of cell doublings over six day period.

Expression of FGF-3 Protein in Bacteria. The 1-2-2 cDNA clone (the complete 1120 base pair EcoRI fragment) of the FGF-3 mRNA was cloned into the EcoRI restriction site of the bacterial expression vector pATH3 (57). The resultant construct, termed pTrpE-FGF-3, will direct synthesis in *E. coli* of a fusion protein containing the bacterial TrpE protein linked to the FGF-3 amino acid sequence. pTrpE-FGF-3 was introduced into *E. coli* HB101, and HB101 carrying pATH3 served as negative control. Five hundred milliliter cultures were harvested and sonicated in five milliliters buffer. Sonicates were clarified by centrifugation, and the soluble extracts were tested for ability to stimulate DNA synthesis in quiescent Balb/c 3T3 cells (protocol described in original manuscript). As shown in Table 6, three microliter of extract from HB101 bearing pTrpE-FGF-3 gives maximal stimulation of DNA synthesis, while comparable volume of extract from HB101 bearing pATH3 has no stimulatory effect. Furthermore, the mitogenic activity in HB101/pTrpE-FGF-3 extracts binds to heparin Sepharose columns and elutes at the same high salt concentrations as the growth factor secreted from NIH 3T3 cells transformed with the FGF-3 gene (pLTR122) (data not shown). Hence, the FGF-3 protein is conclusively shown to be a growth factor active on Balb/c 3T3 fibroblasts.

TABLE 6

Mitogenic activity of bacterial extracts containing FGF-3

| Bacterial Extract | Volume of Extract (microliters) | DNA Synthesis (3H-TdR Incorporation) (c.p.m./1000) |
|---|---|---|
| HB101/pTrpE-FGF-3 | 1 | 105 |
| HB101/pTrpE-FGF-3 | 3 | 140 |
| HB101/pATH3 | 3 | 1.2 |
| NONE | | 1.1 |

REFERENCES

1. Shih, C., Shilo, B. Z., Goldfarb, M. P. Dannenberg, A., Weinberg, R. A. (1979) Proc. Natl. Acad. Sci. USA 76, 5714–5718.
2. Perucho, M., Goldfarb, M. P., Shimizu, K., Lama, C., Fogh, J., Wigler, M. H. (1981). Cell 27, 467–476.
3. Murray, M., Shilo, B., Shih, C., Cowing, D., Hsu, H. W., Weinberg, R. A. (1981) Cell 25, 355–361.
4. Krontiris, T. G., Cooper, G. M. (1981) Proc. Nat. Acad. Sci. USA 78, 1181–1184.
5. Pulciani, S., Santos, E., Lauver, A. V., Long, L. K., Aaronson, S. A., Barbacid, M. (1983) Nature 300, 539–542.
6. Yuasa, Y., Srivastava, S., Dunn, D. Y., Rhim, J. S., Reddy, E. P., Aaronson, S. A. (1983) Nature 303, 775–779.
7. Parade, L. F., Tabin, C. J., Shih, C., Weinberg, R. A. (1982). Nature 297, 474–475.
8. Santos, E., Tronick, S. R., Aaronson, S. A. Pulciani, S., Barbacid, M. (1982) Nature 298, 343–347.
9. Der, C. J., Krontiris, T. G., Cooper, G. M. (1982) Proc. Nat. Acad. Sci. USA 79, 3637–3640.
10. Shimizu, K., Goldfarb, M., Suard, Y., Perucho, M., Li, Y., Kamata, T., Feramisco, J., Stavnezer, E., Fogh, J., Wigler, M. (1983) Proc. Nat. Acad. Sci. USA 80, 2112–2116.
11. Hall, A., Marshall, C. J. Spurr, N. K., Weiss, R. A. (1983) Nature 303, 396–410.
12. Shimizu, K., Nakatsu, Y., Sekiguchi, M. Hokamura, K., Tanaka, K., Terada, M., Sugimura, T. (1985) Proc. Nat. Acad. Sci. USA 82, 5641–5645.
13. Fukui, M., Yamamoto, T., Kawai, S., Maruo, K., Toyoshima, K. (1985) Proc. Nat. Acad. Sci. USA 82, 5954–5948.
14. Eva, A., Aaronson, S. A. (1985) Nature 316, 273–275.
15. Martin-Zanca, D., Hughes, S. H., Barbacid, M. (1986) Nature 319, 743–748.
16. Dean, M., Park, M., LeBeau, M. M., Robins, T. S., Diaz, M. O., Rowley, J. D. Blair, D. G., VandeWoude, G. F. (1985) Nature 318, 385–388.
17. Young, D., Waitches, G., Birchmeier, C., Fasano, O., Wigler, M. (1986) Cell 45, 711–719.
18. Zhan, Z., Goldfarb, M. (1986) Mol. Cell Biol. 6, 3541–3544.
19. Fogh, J. (1978) Nat. Cancer Inst. Monogr. 49, 5–9.
20. Fogh, J., Wright, W. C., Loveless, J. D. (1977) J. Nat. Cancer Inst. 58, 209–214.

21. Fough, J., Fogh, J. M., Orfeo, T. (1977) J. Nat. Cancer Inst. 59, 221-225.
22. Soule, H. D., Vasquez, J., Long, A., Albert, S., Brennan, M. (1973) J. Nat. Cancer Inst. 51, 1409-1416.
23. Takaki, T. (1980) J. Cancer Res. Clin. Oncol. 96, 27-33.
24. Rasheed, S., Gardner, M. B., Rongey, R. W., Nelson-Rees, W. A., Arnstein, P. (1977) J. Nat. Cancer Inst. 58, 881-890.
25. Tanaka, T., Weisblum, B., (1975) J. Bacteriol. 121, 354-362.
26. Yamamoto, K. R., Alberts, B. M., Benzinger, R., Lawhorne, L., Treiber, G. (1970) Virology 40, 734-744.
27. Wigler, M., Sweet, R., Sim, G. K., Wold, B., Pellicer, A., Lacy, E., Maniatis, T., Silverstein, S., Axel, R. (1979) Cell 16, 777-785.
28. Fasano, O., Taparowsky, E., Fiddes, J., Wigler, M., Goldfarb, M. (1983) J. Mol. App. Genet. 2, 173-180.
29. Ellis, R. W., Defeo, D., Shih, T. Y., Gonda, M. A., Young, H. A., Tsuchida, N., Lowy, D. R., Scolnick, E. M. (1981) Nature 292, 506-511.
30. Jelinek, W. R., Tooney, T. P., Leinwand, L., Duncan, C. H., Biro, P., Choudary, A., Weissman, P. V., Rubin, S. M., Houch, C. M. Deninger, P. L., Schmid, C. W. (1980) Proc. Nat. Acad. Sci. USA 77, 1398-1402.
31. Melton, D. A., Kreig, P. A., Rebagliati, M. R., Maniatis, T., Zinn, K., Green, M. R. (1984) Nuc. Acid Res. 12, 7035-7056.
32. Southern, E. M. (1975) J. Mol. Biol. 98, 503-517.
33. Maniatis, T., Jeffrey, A., Kleid, D. G. (1975) Proc. Nat. Acad. Sci. USA 72, 1184-1188.
34. Thomas, P. S. (1980) Proc. Nat. Acad. Sci. USA 77, 5501-5505.
35. Sharp, P. A., Gallimore, P. H., Flint, S. J (1974) Cold Spring Harbor Sympos. Quant. Biol. 39, 457-474.
36. Hohn, B., Murray, K. (1977) Proc. Nat. Acad. Sci. USA 74, 3259-3263.
37. Benton, W., Davis, R. (1977) Science 196, 180-182.
38. Gubler, U., Hoffman, B. J. (1983) Gene 25, 263-269.
39. Fasano, O., Birbaum, D., Edlund, L., Fogh, J., Wigler, M. (1984) Mol. Cell. Biol. 4:1695-1705.
40. Gimenez-Gallego, G., Rodkey, J., Bennett, C., Rios-Candelore, M., DiSalvo, J., Thomas, K. (1985) Science, 230, 1385-1388.
41. Abraham, J. A., Mergia, A., Whang, J. L., Tumolo, A., Friedman, J., Hjerrild, K. A., Gospodarowicz, D., Fiddes, J. C. (1986) Science, 233, 545-548.
42. Moore, R., Casey, G., Brookes, S., Dixon, M., Peters, G., Dickson, C. (1986) EMBO, 5, 919∝924.
43. Taira, M., Yoshida, T., Miyagawa, K., Sakamoto, H. Terada, M., Sugimura, T. (1987) Proc. Nat. Acad. Sci. USA 84, 2980-2984.
44. Wigler, M., et al. (1979) Cell, 16, 777-785.
45. Zahn, X., Culpepper, A., Reddy, M., Loveless, J., Goldfarb, M. (1987), Oncogene 1: 369-376
46. J. C. Gospadarowicz, D. (187), Nature 325, 257-259.
47. Sanger, F., Nicklen, S., Coulson, A. R. (1977), Proc. Nat. Acad. Sci. USA 74, 5463-5467.
48. Reth, M., Alt, F. (1984), Nature 312, 418-423.
49. Pledger, W. J., Stiles, C. D., Antoniades, H. N., Scher, C. D. (1977), Proc. Nat. Acad. Sci. USA 74, 4481-4485.
50. Maciag, T., Mehlman, T., Freisel, R., Schreiber, A. (1984), Science 225, 932-935.
51. Shing, Y., Folkman, J., Sullivan, R. M Butterfield, C., Murray, J., Klagsburn, M. (1984), Science 223, 1296-1299.
52. Conn, G., Hatcher, V. B. (1984), Biochem. Biophys. Common. 124, 262-268.
53. Blobel, G., Walter, P., Change, G. N., Goldman, B. M., Erickson, A. H., Lingappa, V. R. (1979), Symp. Soc. Exp. Biol. 33, 9-36.
54. Yoshida, T., Miyagawa, K., Odagiri, H., Sakamoto, H., Little, P. F. R., Terada, M., Sugimura, T. (1987), Proc. Nat. Acad. Sci. USA 84, 7305-7309.
55. Moore, R., Casey, G., Brookes, S., Dixon, M., Peters, G., Dickson, C. (1986), EMBO J. 5, 919-924.
56. Abraham, J., Mergia, A., Whang, J. L., Tumulo, A., Friedman, J., Hjerrild, K. A., Gospadarowicz, D., Fiddes, J. C. (1986), Science 233, 545-548.
57. Tanese, et al., J. Virology (1986) 59: 328.

What is claimed is:

1. A purified polypeptide having the amino acid sequence shown in FIG. 5 for ORF-2.

2. A method of stimulating the proliferation of mesodermal cells comprising contacting the mesodermal cells with an effective mesodermal cell proliferating amount of a composition comprising the polypeptide of claim 1, thereby stimulating the proliferation of mesodermal cells.

3. A method of claim 2, wherein the mesodermal cells are vascular endothelial cells.

4. A method of stimulating capillary growth comprising contacting the capillaries with an effective capillary stimulating amount of a composition comprising the polypeptide of claim 1, thereby stimulating capillary growth.

5. A method of promoting tissue repair in a subject with damaged tissue comprising contacting the damaged tissue with an effective tissue repairing amount of a composition comprising the polypeptide of claim 1, thereby promoting tissue repair in a subject with damaged tissue.

6. A purified polypeptide having the amino acid sequence shown in FIG. 5 for ORF-1.

* * * * *